US00PP27324P2

(12) United States Plant Patent
Hartmann

(10) Patent No.: US PP27,324 P2
(45) Date of Patent: Nov. 1, 2016

(54) BLUEBERRY PLANT NAMED 'ANTHOCYANIN BLUES'

(50) Latin Name: *Vaccinium corymbosum*
Varietal Denomination: Anthocyanin Blues

(71) Applicant: Patrick Edward Hartmann, Lacota, MI (US)

(72) Inventor: Patrick Edward Hartmann, Lacota, MI (US)

(73) Assignee: Cynthia Hartmann, Lacota, MI (US)

( * ) Notice: Subject to any disclaimer, the term of this patent is extended or adjusted under 35 U.S.C. 154(b) by 109 days.

(21) Appl. No.: 14/121,304

(22) Filed: Aug. 18, 2014

(51) Int. Cl.
*A01H 5/08* (2006.01)

(52) U.S. Cl.
USPC ..... Plt./157

(58) Field of Classification Search
USPC ..... Plt./157
See application file for complete search history.

*Primary Examiner* — Keith Robinson
(74) *Attorney, Agent, or Firm* — Penny J. Aguirre

(57) ABSTRACT

A new cultivar of Blueberry plant, 'Anthocyanin Blues', that is characterized by its berries that are very small in size, dark blue in color in small compact clusters and are very firm, pleasant tasting, do no leak juice, promote molds, have a long shelf life, its berries with an early ripening season that 90% of the berries can be harvested in a single pick by machine harvesting, its berries that have a small dry picking scar and can be harvested without stems attached, its resistance to berry molds, its upright growth habit with moderate branching and numerous canes with small dark green leaves, and its lack of rooting suckers.

2 Drawing Sheets

Botanical classification: *Vaccinium corymbosum.*
Cultivar designation: 'Anthocyanin Blues'.

BACKGROUND OF THE INVENTION

The present invention relates to a new and distinct cultivar of *Vaccinium corymbosum*, and will be referred to hereafter by its cultivar name, 'Anthocyanin Blues'. 'Anthocyanin Blues' is a new cultivar of Northern highbush blueberry plant grown for fruit production.

The Inventor discovered the new cultivar in July of 2000 as a chance seedling that was growing in a production field in Grand Junction, Mich. that was established in the late 1960s and contained numerous varieties of *Vaccinium corymbosum*. The parentage is unknown.

Asexual propagation of the new cultivar was first accomplished by the Inventor by hardwood stem cuttings in Watervliet, Mich. in spring of 2004. Asexual propagation by hardwood stem cuttings has determined that the characteristics of this cultivar are stable and are reproduced true to type in successive generations.

SUMMARY OF THE INVENTION

The following traits have been repeatedly observed and represent the characteristics of the new cultivar, which in combination distinguish 'Anthocyanin Blues' as a new and distinct cultivar of blueberry.

1. 'Anthocyanin Blues' exhibits berries that are very small in size; an average of 1,400 berries/lb.
2. 'Anthocyanin Blues' exhibits berries that are dark blue in color in small compact clusters and are very firm, pleasant tasting, do no leak juice, or promote molds.
3. 'Anthocyanin Blues' exhibits berries with an extra shelf life; up to 3 months when refrigerated.

4. 'Anthocyanin Blues' exhibits an early ripening season and about 90% of the berries can be harvested in a single pick by machine harvesting.
5. 'Anthocyanin Blues' exhibits berries that have a small dry picking scar and can be harvested without stems attached.
6. 'Anthocyanin Blues' exhibits resistance to berry molds caused by *Anthracnose* sp. and *Alternaria* sp.
7. 'Anthocyanin Blues' exhibits an upright growth habit with moderate branching and numerous canes with small dark green leaves.
8. 'Anthocyanin Blues' does not produce rooting suckers (unless covered by soil).

'Anthocyanin Blues' can also be most closely compared to the cultivars 'Little Giant' (not patented) and 'Rubel' (not patented). Both are similar to 'Anthocyanin Blues' in having small fruit. 'Little Giant' differs from 'Anthocyanin Blues' in having larger berries, in producing suckers that root, and in requiring multiple harvest times. 'Rubel' differs from 'Anthocyanin Blues' in having larger fruit, larger leaves and in having fruit that does not ripen uniformly and requires multiple pickings.

BRIEF DESCRIPTION OF THE DRAWINGS

The accompanying colored photographs illustrate the overall appearance and distinct characteristics of the new blueberry. The photographs were taken of a plant about five years in age as field grown outdoors in Grand Junction, Mich.

The photograph in FIG. 1 provides a view of the plant habit of 'Anthocyanin Blues'.

Figure 1:
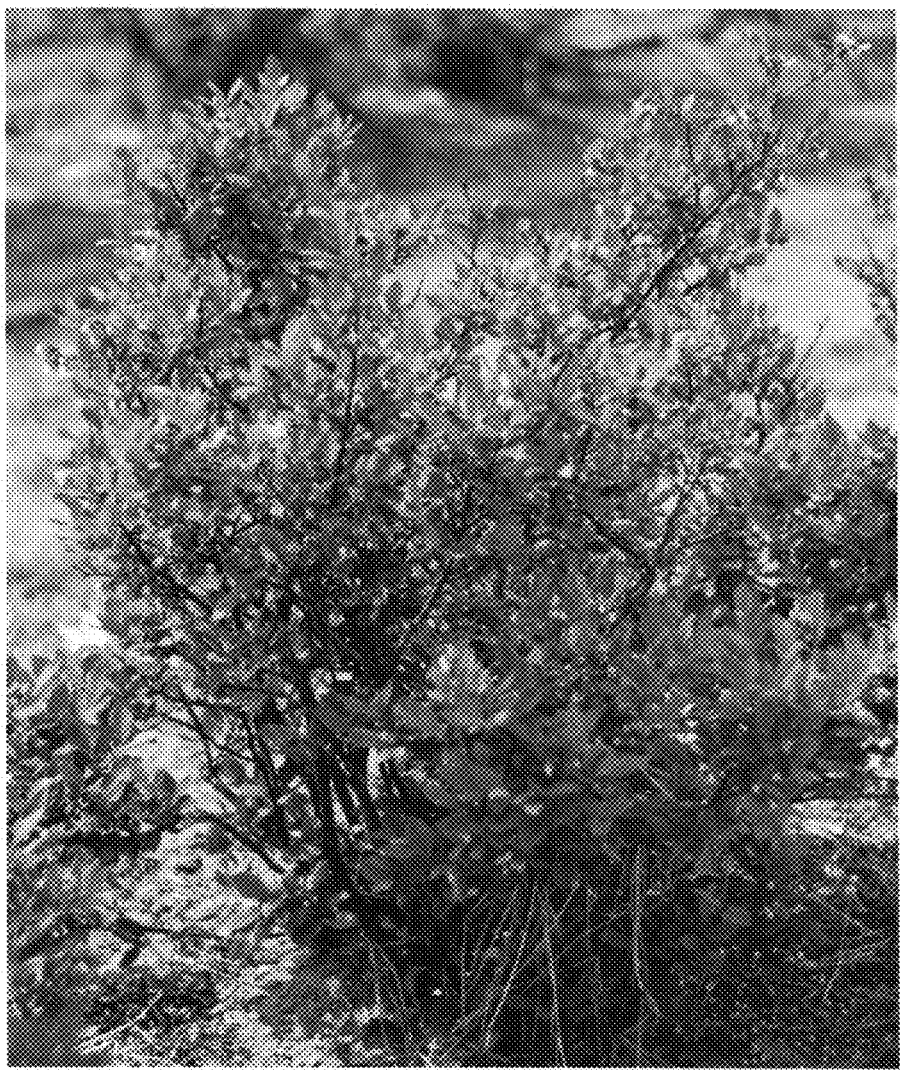
Figure 2:
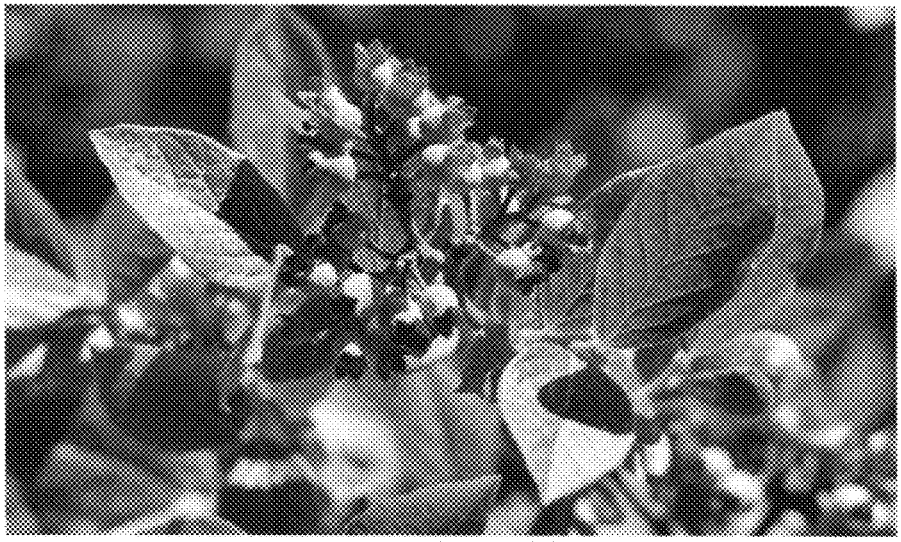

The photograph in FIG. 2 provides a close-up view of a developing fruit cluster.

Figure 3:
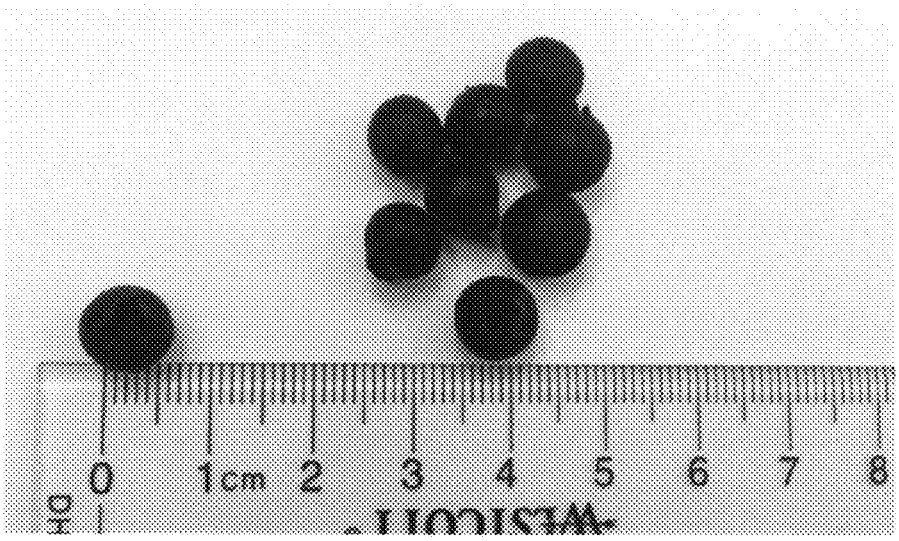

The photograph in FIG. 3 provides a close-up view of mature fruit of 'Anthocyanin Blues'.

The colors in the photographs may differ slightly from the color values cited in the detailed botanical description, which accurately describe the colors of the new Blueberry.

DETAILED BOTANICAL DESCRIPTION OF THE PLANT

The following is a detailed description of three year-old plants of the new cultivar grown outdoors in 1-gallon containers in Grand Junction, Mich. with data concerning mature plants taken from plants five years in age as field grown in Grand Junction, Mich. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used General plant characteristics:

*Plant type.*—Deciduous shrub, fruit producing.

*Plant habit.*—Upright, moderately branched with numerous canes.

*Height and spread.*—Reaches 1.2 to 1.5 m (4 to 5 ft.) in height and an average of 91 cm (36 in.) in spread.

*Cold hardiness.*—At least U.S.D.A. Zone 4, some winter injury has been observed at temperatures of −20° F., but only when grown in wet areas.

*Disease resistance.*—Good resistance has been observed to infection by *Anthracnose* sp. and *Alternaria* sp. (berry molds).

*Root description.*—Fibrous.

*Suckering.*—Suckers have not been observed to root except if covered with soil.

*Growth rate.*—Moderate.

*Propagation.*—Hardwood stem cuttings.

Stem description (mature plant):

*Mature canes.*—A blend of 197C, 165A and N200C in color, an average of 1.2 m in length and 1.5 cm in width on a mature plant, bark surface changes from smooth to bark-like.

*Dormant stems (previous years growth).*—Mature plant; 172A in color, average of 15 cm in length and 2.4 mm in width, surface is glabrous.

*New growth.*—144A to 144B in color.

*Branching.*—Moderate with numerous canes.

Stem description (one-gallon container):

*Stem size.*—Lateral branches are an average of 28 cm in length and 5 mm in width, secondary branches; an average of 10 cm in length and 2 mm in width.

*Stem color.*—Young shoots; 144A to 144B, 144A, bark at base is a blend of 197C, 165A and N200C in color.

*Internode length.*—Average of 2 cm.

*Branching habit.*—An average of 2 lateral branches from the base, with an average of 10 secondary branches on a 1-gallon pot.

*Branching aspect.*—Lateral branches upright to 20°, secondary branches; upright to an angle of 45°.

Foliage description:

*Leaf shape.*—Narrowly ovate.

*Leaf division.*—Simple.

*Leaf base.*—Acute.

*Leaf apex.*—Acute.

*Leaf venation.*—Pinnate.

*Leaf margins.*—Entire.

*Leaf attachment.*—Petiolate.

*Leaf arrangement.*—Alternate.

*Leaf surface.*—Smooth, upper surface moderately glossy and slightly rugose, lower surface matte.

*Leaf color.*—Young upper and lower surface; N144A, mature upper surface: N137A, mature lower surface; 137B.

*Leaf size.*—Average of 6 cm in length and 3 cm in width.

*Leaf aspect.*—Held horizontal to upward at about a 45° angle.

*Leaf fragrance.*—None.

*Leaf veins.*—Upper and lower surfaces similar to leaf color.

*Petioles.*—Round in shape, an average of 3 mm in length and 1.5 mm in width, 144B in color, glabrous surface.

*Stipules.*—None observed.

*Synchrony of leafing and flowering.*—Flowers are well exposed, leaves expand after bloom.

Inflorescence description:

*Bloom season.*—Late April (buds form) to petal drop about the end of May in Michigan (depending on annual conditions).

*Inflorescence.*—Compact cluster, an average of 1 cm in length and 1.9 cm in width.

*Lastingness of inflorescence.*—Average of 8 days but highly dependent on temperatures.

*Number of flowers.*—An average of 10 per inflorescence (cluster).

*Flower fragrance.*—None.

*Flower size.*—An average of 8 mm in length and 6 mm in width.

*Flower buds.*—Ovate to elliptic in shape, an average of 8 mm in length and 4.5 mm in width, color; a blend of 155A and 157C, lightly suffused with 150C at the tip.

*Corolla.*—Urceolate in shape, comprised of 5 fused petals, an average of 7 mm in length and 5.5 mm in width, aperture is an average of 2 mm in diameter, free apex is subacute and reflexed, color; inner surface a blend of NN155C and 157C, outer surface a blend of 155C and 157C, with outer surface becoming tinged with 186D (186A at apex) with sun exposure, smooth and glabrous texture on both surfaces.

*Calyx.*—Campanulate, comprised of 5 fused sepals with lobes free at apex, an average of 3.5 mm in length and 4 mm in width at anthesis, color; inner surface 144B and outer surface apical half 144B and basal half 144A, surface glabrous and smooth.

*Pedicels.*—Round, an average of 2.5 mm in length and 1 mm in width, 144A in color, smooth and glabrous surface.

*Peduncles.*—Round, an average of 5 mm in length and 1 mm in width, 144A in color, surface is glabrous.

Reproductive organs:

*Androecium.*—About 10 stamens, an average of 3 mm in length, basifixed anthers are an average of 1 mm in length and 165B in color, filaments are an average of 2 mm in length and 165C in color, pollen is very low in abundance and 165B in color.

*Gynoecium.*—1 pistil, flattened stigma is minute in size and 144C in color, style is linear in shape, an average of 5.5 mm in length and 0.8 mm in width, and 144D in color, ovary is 144A in color.

Fruit description:

*Type.*—Berry.

*Number.*—Average of 16 per cluster.

*Cluster tightness.*—Compact.

*Fruit size.*—Very small, up to 8 mm in diameter and length.

*Skin color.*—Immature 143B, mid-maturity a blend between 143B, 183A and 177A, mature 103A.

*Date of fruit ripening.*—Early, around July 15$^{th}$ in S.W. Michigan.

*Skin surface.*—Low to medium level of glaucous coating (bloom).

*Shape.*—Globose.

*Flesh color.*—Immature 143C, mature 156A.

*Flesh texture.*—Fleshy.

*Calyx lobes.*—Average of 1 mm in length and 1.5 mm in width, triangular in shape.

*Calyx diameter of aperture.*—Average of 3 mm.

*Scar size.*—Small and dry.

*Flavor.*—Sweet taste.

*Firmness.*—Very firm.

*Weight.*—1,400 berries/lb.

*BRIX.*—12.5°.

*pH.*—4.2.

*Productivity.*—High.

*Storage life.*—Up to 3 weeks in refrigeration (~3° C.).

*Fruit use.*—Fresh fruit and processed fruit products.

*Seed.*—Oblong to oval in shape, average of 10 per fruit, <1 mm in length and width, color; immature 150D, mature 53A.

It is claimed:

1. A new and distinct cultivar of Blueberry plant named 'Anthocyanin Blues' as herein illustrated and described.

* * * * *